(12) United States Patent
Schneider et al.

(10) Patent No.: US 7,896,911 B2
(45) Date of Patent: Mar. 1, 2011

(54) DEVICE AND METHOD FOR TACKING PLAQUE TO BLOOD VESSEL WALL

(75) Inventors: Peter Schneider, Honolulu, HI (US); Robert Giasolli, Orange, CA (US)

(73) Assignee: Innovasc LLC, Honolulu, HI (US)

( * ) Notice: Subject to any disclaimer, the term of this patent is extended or adjusted under 35 U.S.C. 154(b) by 465 days.

(21) Appl. No.: 11/955,331

(22) Filed: Dec. 12, 2007

(65) Prior Publication Data

US 2009/0157159 A1    Jun. 18, 2009

(51) Int. Cl.
 *A61F 2/06* (2006.01)
(52) U.S. Cl. .................................. 623/1.11; 623/1.15
(58) Field of Classification Search .................. None
 See application file for complete search history.

(56) References Cited

U.S. PATENT DOCUMENTS

| | | | |
|---|---|---|---|
| 3,221,746 A | 12/1965 | Noble | |
| 3,635,223 A | 1/1972 | Klieman | |
| 4,465,072 A | 8/1984 | Taheri | |
| 5,009,659 A | 4/1991 | Hamlin | |
| 5,042,707 A | 8/1991 | Taheri | |
| 5,196,024 A | 3/1993 | Barath | |
| 5,336,234 A | 8/1994 | Vigil | |
| 5,423,851 A | 6/1995 | Samuels | |
| 5,501,689 A | 3/1996 | Green | |
| 5,569,272 A | 10/1996 | Reed | |
| 5,616,149 A | 4/1997 | Barath | |
| 5,665,116 A | 9/1997 | Chaisson | |
| 5,681,346 A | 10/1997 | Orth | |
| 5,797,951 A | 8/1998 | Mueller | |
| 5,800,526 A | 9/1998 | Anderson | |
| 6,007,543 A | 12/1999 | Ellis | |
| 6,036,725 A * | 3/2000 | Avellanet | 623/1.13 |
| 6,053,943 A | 4/2000 | Edwin | |
| 6,126,685 A * | 10/2000 | Lenker et al. | 623/1.11 |
| 6,197,013 B1 | 3/2001 | Reed | |
| 6,290,728 B1 * | 9/2001 | Phelps et al. | 623/23.7 |
| 6,371,962 B1 | 4/2002 | Ellis | |
| 6,475,237 B2 | 11/2002 | Drasler | |
| 6,942,680 B2 | 9/2005 | Grayz | |
| 7,007,698 B2 * | 3/2006 | Thornton | 128/898 |
| 7,087,088 B2 * | 8/2006 | Berg et al. | 623/23.64 |

(Continued)

*Primary Examiner*—Eduardo C Robert
*Assistant Examiner*—Christopher Schubert
(74) *Attorney, Agent, or Firm*—Leighton K. Chong

(57) ABSTRACT

A plaque tack device for treating atherosclerotic occlusive disease is formed as a thin, annular band of durable, flexible material having a plurality of barbs or anchoring points on its outer periphery for preventing it from being dislodged. The plaque tack may be used with a balloon angioplasty procedure or as a de novo treatment for blood vessel blockage to reopen the vessel lumen for desired blood flow. It has a width that is small relative to its diameter, to minimize the amount of foreign structure placed in the blood vessel. One or more tacks may be applied in positions along a plaque accumulation site as needed to stabilize the site and/or hold pieces of plaque out of the way of blood flow. The barbs of the tack may be pressed into the plaque and/or blood vessel walls by balloon expansion. Related methods of deployment and delivery devices are provided for insertion of the plaque tack in a compressed state into the blood vessel and expanding it back to its annular shape for holding plaque against the blood vessel walls.

7 Claims, 17 Drawing Sheets

U.S. PATENT DOCUMENTS

| | | |
|---|---|---|
| 7,179,284 B2 | 2/2007 | Khosravi |
| 7,211,101 B2 * | 5/2007 | Carley et .................. 606/213 |
| 7,270,673 B2 | 9/2007 | Yee |
| 7,303,572 B2 | 12/2007 | Meisheimer |
| 2003/0158595 A1 * | 8/2003 | Randall et al. ............. 623/1.13 |
| 2004/0143287 A1 | 7/2004 | Konstantino |
| 2004/0186551 A1 | 9/2004 | Kao et al. |
| 2005/0288764 A1 * | 12/2005 | Snow et al. ................ 623/1.11 |

* cited by examiner

DEVICE AND METHOD FOR TACKING PLAQUE TO BLOOD VESSEL WALL

TECHNICAL FIELD

This invention relates to treatment of atherosclerotic occlusive disease by intravascular procedures for pushing and holding plaque accumulated on the blood vessel walls out of the way for reopened blood flow.

BACKGROUND OF INVENTION

Atherosclerotic occlusive disease is the primary cause of stroke, heart attack, limb loss, and death in the US and the industrialized world. Atherosclerotic plaque forms a hard layer along the wall of an artery and is comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty.

Balloon angioplasty is an accepted method of opening blocked or narrowed blood vessels in every vascular bed in the body. Balloon angioplasty is performed with a balloon angioplasty catheter. The balloon angioplasty catheter consists of a cigar shaped, cylindrical balloon attached to a catheter. The balloon angioplasty catheter is placed into the artery from a remote access site that is created either percutaneously or through open exposure of the artery. The catheter is passed along the inside of the blood vessel over a wire that guides the way of the catheter. The portion of the catheter with the balloon attached is placed at the location of the atherosclerotic plaque that requires treatment. The balloon is inflated to a size that is consistent with the original diameter of the artery prior to developing occlusive disease. When the balloon is inflated, the plaque is broken. Cleavage planes form within the plaque, permitting the plaque to expand in diameter with the expanding balloon. Frequently, a segment of the plaque is more resistant to dilatation than the remainder of the plaque. When this occurs, greater pressure pumped into the balloon results in full dilatation of the balloon to its intended size. The balloon is deflated and removed and the artery segment is reexamined. The process of balloon angioplasty is one of uncontrolled plaque disruption. The lumen of the blood vessel at the site of treatment is usually somewhat larger, but not always and not reliably.

Some of the cleavage planes created by fracture of the plaque with balloon angioplasty form dissection. A dissection occurs when a portion of the plaque is lifted away from the artery and is not fully adherent and may be mobile or loose. The plaque that has been disrupted by dissection protrudes into the flowstream. If the plaque lifts completely in the direction of blood flow, it may impede flow or cause acute occlusion of the blood vessel. There is evidence that dissection after balloon angioplasty must be treated to prevent occlusion and to resolve residual stenosis. There is also evidence that in some circumstances, it is better to place a metal retaining structure, such as stent to hold open the artery after angioplasty and force the dissected material back against the wall of the blood vessel to create an adequate lumen for blood flow.

Therefore, the clinical management of dissection after balloon angioplasty is currently performed primarily with stents. As illustrated in FIG. 24A, a stent is a tube having a diameter that is sized to the artery. A stent is placed into the artery at the location of a dissection to force the dissection flap against the inner wall of the blood vessel. Stents are usually made of metal alloys. They have varying degrees of flexibility, visibility, and different placement techniques. Stents are placed in every vascular bed in the body. The development of stents has significantly changed the approach to minimally invasive treatment of vascular disease, making it safer and in many cases more durable. The incidence of acute occlusion after balloon angioplasty has decreased significantly with stents.

However, stents have significant disadvantages and much research and development is being done to address these issues. Stents induce repeat narrowing of the treated blood vessel (recurrent stenosis). Recurrent stenosis is the "Achilles heel" of stenting. Depending on the location and the size of the artery, in-growth of intimal hyperplastic tissue from the vessel wall directly through the tines or openings in the stent may occur and cause failure of the vascular reconstruction by narrowing or occlusion of the stent. This may occur any time after stent placement. In many cases, the stent itself seems to incite local vessel wall reaction that causes stenosis, even in the segment of the stent that was placed over artery segments that were not particularly narrowed or diseased during the original stent procedure. This reaction of the blood vessel to the presence of the stent is likely due to the scaffolding effect of the stent. This reaction of recurrent stenosis or tissue in growth of the blood vessel is in response to the stent. This activity shows that the extensive use of metal and vessel coverage in the artery as happens with stenting is contributing to the narrowing. The recurrent stenosis is a problem because it causes failure of the stent and there is no effective treatment. Existing treatment methods that have been used for this problem include; repeat angioplasty, cutting balloon angioplasty, cryoplasty, atherectomy, and even repeat stenting. None of these methods have a high degree of long-term success.

Stents may also fracture due to material stress. Stent fracture may occur with chronic material stress and is associated with the development of recurrent stenosis at the site of stent fracture. This is a relatively new finding and it may require specialized stent designs for each application in each vascular bed. Structural integrity of stents remains a current issue for their use. Arteries that are particularly mobile, such as the lower extremity arteries and the carotid arteries, are of particular concern. The integrity of the entire stent is tested any time the vessel bends or is compressed anywhere along the stented segment. One reason why stent fractures may occur is because a longer segment of the artery has been treated than is necessary. The scaffolding effect of the stent affects the overall mechanical behavior of the artery, making the artery less flexible. Available stenting materials have limited bending cycles and are prone to failure at repeated high frequency bending sites.

Many artery segments are stented even when they do not require it, thereby exacerbating the disadvantages of stents. There are several reasons for this. Many cases require more than one stent to be placed and often several are needed. Much of the stent length is often placed over artery segments that do not need stenting and are merely adjoining an area of dissection or disease. Stents that are adjusted to the precise length of the lesion are not available. When one attempts to place multiple stents and in the segments most in need of stenting, the cost is prohibitive since installation and material is required per stent. The time it takes to do this also adds to the cost and risk of the procedure. The more length of artery that receives a stent that it does not need, the more stiffness is conferred to the artery, and the more scaffolding affect occurs. This may also help to incite the arterial reaction to the stent that causes recurrent stenosis.

SUMMARY OF INVENTION

In accordance with the present invention, a device (and related method of deployment) for treating atherosclerotic occlusive disease comprises a thin, annular band of durable, flexible material (a "plaque tack") having a plurality of barbs or anchoring elements on its outer annular periphery, which is installed intravascularly in one or more specific positions of a plaque accumulation site. The plaque tack is dimensioned and designed to be applied with a spring force against the plaque to press and hold it against the blood vessel walls. The barbs or anchoring elements are embedded into or at least emplaced in physical contact against the plaque by the spring force so that the plaque tack is retained securely in position from being dislodged. The plaque tack is generally used after a balloon angioplasty procedure to reopen the vessel lumen for desired blood flow. The annular band of the plaque tack has a width in the axial direction of the vessel walls that is less than its diameter, in order to minimize the emplacement of foreign scaffolding structure in the blood vessel. One or more tacks are applied only in positions along the length of a plaque accumulation site where specific holding forces are needed to stabilize the site and/or hold pieces of plaque out of the way of blood flow. The barbs or anchor points of the tack(s) may be pressed with an expansion force into the plaque and/or vessel walls by a post-installation balloon expansion procedure.

In the present invention, the plaque tack device is designed as a minimally invasive approach to tacking loose or dissected atherosclerotic plaque to the wall of the artery, as illustrated in FIG. 24B. It may be used to treat either de novo atherosclerotic lesions or the inadequate results of balloon angioplasty. It is designed to maintain adequate lumen in a treated artery without the inherent disadvantages of vascular stents. The device may also be used to administer medications, fluid, or other treatment ("eluting") agents into the atherosclerotic plaque or the wall of the blood vessel or into the bloodstream.

The plaque tack and installation procedure may be designed in a number of ways that share a common methodology of utilizing the spring force of a spring-like annular band to enable the tack to be compressed, folded, or plied to take up a small-diameter volume so that it can be moved into position in the blood vessel on a sheath or catheter, then released, unfolded or unplied to expand to its full diametral size within the blood vessel walls.

In a first embodiment, the plaque tack is formed as a thin, elastically pliable ribbon having a row of pointed cutouts formed on an outward side along its longitudinal length. It can be made of a corrosion-resistant metal or durable polymer. A preferred material is a metal having "shape-memory" (such as Nitinol) which allows it to be formed initially with an annular shape prior to forming in a linear shape, then resume its annular shape when exposed for a length of time at internal body temperature. The ribbon tack can be delivered in linear form carried on a delivery head of a catheter or sheath to the desired position in the blood vessel and pushed along a curved tunnel into its annular shape at the plaque site. The ribbon tack in its annular shape presses against the plaque with a spring force, and remains in the annular shape due to its shape-memory at internal body temperature. When deployed in its annular shape, the row of tongues of cutout points are opened and exposed to point outwardly from the now curved surface of the annular band, so that they can be embedded into or at least emplaced frictionally against the plaque to prevent the tack from becoming dislodged.

In a second embodiment, the plaque tack is formed as a folding ring tack having V-shaped segments for folding and inverted-V-shaped points. The V-shaped segments allow the ring to be radially compressed to a small-diameter volume for carriage in a deployment tube on the end of the sheath. At the desired position, the compressed ring tack is released from the deployment tube so that the ring springs out to its full diametral shape and the outward points act as barb or anchor points embedded into or pressed against the plaque.

In a third embodiment, the plaque tack is formed as a flexible ring of pliable material having an array of outer barbs on an outward side of the ring, and an array of inner radial fingers, wherein the array of fingers are used to displace the outer barbs to lie horizontally flat in one axial direction when the fingers are pushed in the opposite axial direction. With the outer barbs displaced to lie horizontally flat, the flexible ring can be loaded on the outer surface of a catheter delivery tube and held down by a retainer element to allow insertion into the blood vessel. The fingers are removed so that they are not present to obscure the blood vessel when the tack is installed. At the desired position, the retainer element is displaced to release the flexible ring tack to spring up with its barbs extending radially outwardly for embedding into the plaque.

In a fourth embodiment, the plaque tack is formed as a annular band in a coil shape with opposite ends unjoined. The ends are pulled in opposite directions to flatten the coil tack in a tight spiral to reduce its cross-section to a smaller-diameter volume for loading on a catheter delivery tube while being held down by a shell or cover for insertion in the blood vessel. At the desired position in the blood vessel, the cover is displaced to release the tack and allow it to expand back to its full annular shape in position against the plaque.

In a fifth embodiment, the plaque tack is formed as a compressible wire mesh tack with barbs formed on its outer surface. The wire mesh tack can be compressed to reduce its cross-section to a smaller-diameter volume so that it can be loaded on a catheter delivery tube held down by a cover or shell for insertion in the blood vessel. At the desired position in the blood vessel, the shell is displaced to release the tack and allow it to expand back to its full annular shape in position against the plaque.

The plaque tack solves the problems associated with stents by being placed only in areas of plaque that require a holding force. Its minimal axial length enables less scaffolding structure to be used in the artery than with typical stents, and thereby may incite less body reaction and less recurrent stenosis. Only segments of the artery that need treatment are covered and healthy arteries are not treated. The tack is designed for tacking or embedding into the artery wall which is more advantageous than requiring deployment of a "sleeve" type of length associated with stenting. A small amount of foreign body contact with the blood stream and the wall of the artery will incite less reaction. The tack occupies only a narrow section of the artery, thereby limiting bending stresses on the tack as seen in the failure modes of stents. The plaque tack covers a very short distance and does not affect the overall mechanical properties of an entire segment of artery. The material stress will be much less than that on a stent that has to scaffold the entire artery segment. The simplicity of the plaque tack design allows it to be made at lower material and fabrication cost, and to avoid excessive joints or welded points of the type that can weaken a stent structure.

Other objects, features, and advantages of the present invention will be explained in the following detailed description of the invention having reference to the appended drawings.

DETAILED DESCRIPTION OF INVENTION

Figure 1A:
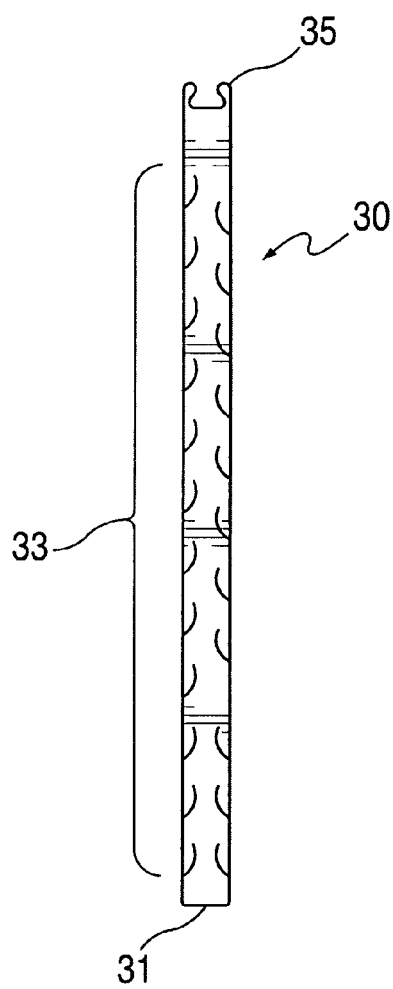
FIGS. 1A and 1B are schematic diagrams of a first embodiment in ribbon form for the plaque tack device of the present invention.

In the following detailed description of the invention, certain preferred embodiments are illustrated providing certain specific details of their implementation. However, it will be recognized by one skilled in the art that many other variations and modifications may be made given the disclosed principles of the invention. Reference for the description is made to the accompanying drawings, wherein like reference numerals refer to similar parts throughout the several views.

Figure 24A:
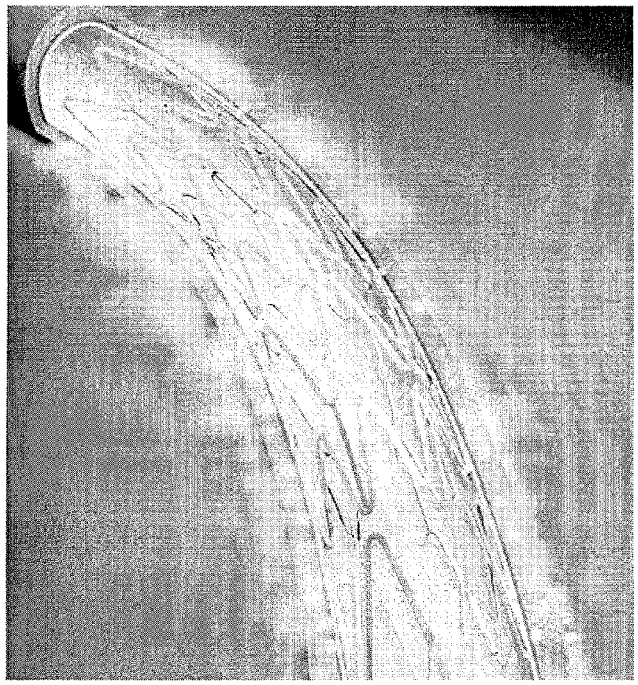
FIG. 24A illustrates the use of a stent installed after angioplasty as conventionally practiced in the prior art.
Figure 24B:
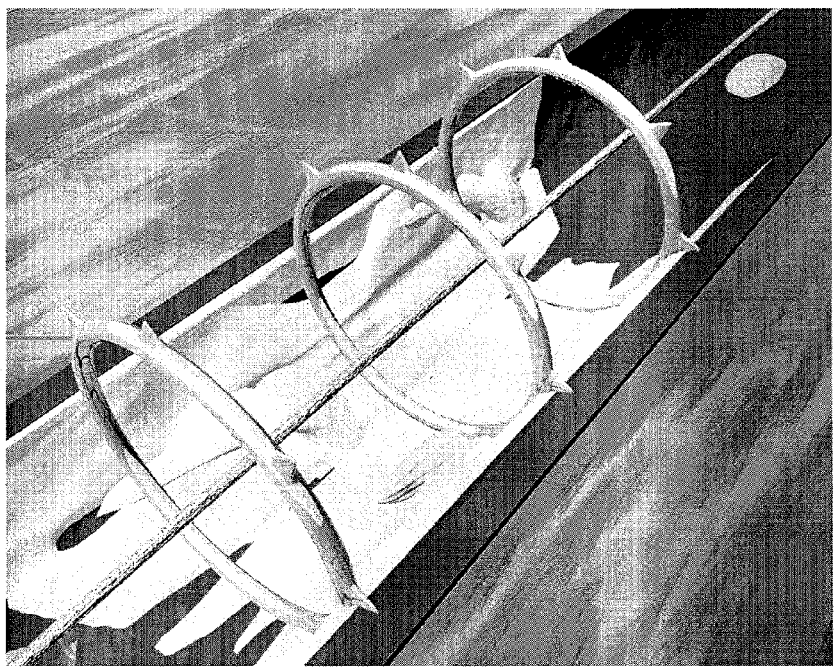
FIG. 24B illustrates the use of the plaque tack installed after angioplasty demonstrating its advantages over the prior art.

As illustrated in FIG. 24B, the plaque tack device in the present invention generally comprises a thin, annular band of durable, flexible material having a plurality of barbs or anchoring elements on its outer annular periphery. The plaque tack is dimensioned diametrically and is designed to be applied with a spring force against the plaque to press and hold it against the blood vessel walls. The barbs or anchoring elements are embedded into or at least emplaced in physical contact against the plaque by the spring force of the plaque tack. The plaque tack extends over only a small area in the axial direction of the vessel walls, in order to minimize the amount of foreign structure placed in the blood vessel. One or more tacks are applied only in positions along the length of a plaque accumulation site where specific holding forces are needed to stabilize the site and/or hold pieces of plaque out of the way of blood flow.

The plaque tack and installation procedure may be designed in a number of ways that share a common methodology of utilizing the spring force of a spring-like annular band to enable the tack to be compressed, folded, or plied to take up a small-diameter volume so that it can be moved into position in the blood vessel on a sheath or catheter, then released, unfolded or unplied to expand to its full-diametral size within the blood vessel walls.

Figure 1B:
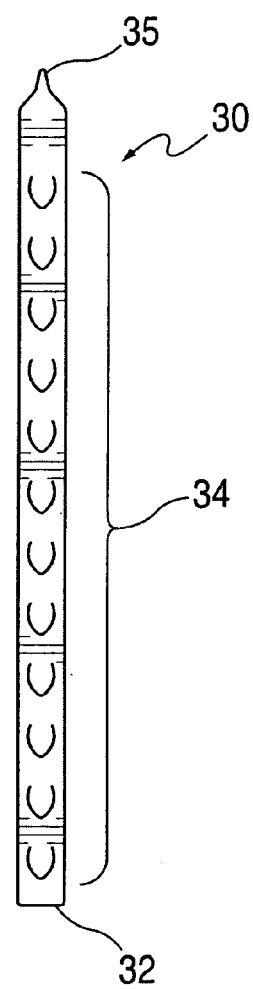
Figure 2:
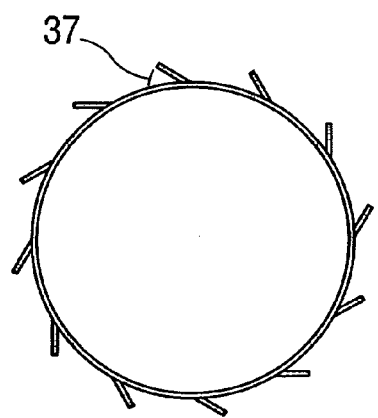
FIG. 2 is a side view of the first embodiment of the ribbon tack of FIG. 1B in its annular shape after deployment.

In the following description, five general embodiments of the plaque tack device and how to deliver it are explained in detail, referred to as: (1) ribbon tack; (2) folding ring tack; (3) flexible ring tack; (4) spiral coil tack; and (5) wire mesh tack. All these embodiments are delivered into the blood vessel from endovascular insertion. The delivery device for each involves a delivery apparatus that has some features of a vascular sheath. The delivery device for each is different and has features that are specifically designed to deliver the specific tack Referring to FIGS. 1A and 1B, a first preferred embodiment of the plaque tack device is shown in two versions of a ribbon tack, each having a linear, flat shape like a ribbon. The version in FIG. 1A has a base end 31, rows 33 of cutout tongues or apertured portions that open out as pointed barbs or anchors, and a retainer end 35. The version in FIG. 1B has a base end 32, single row 34 of cutout portions that open out as pointed barbs or anchors, and a retainer end 35. Each version may be made of a material such as a corrosion-resistant metal, polymer, composite or other durable, flexible material. A preferred material is a metal having "shape-memory" (such as Nitinol) which allows it to be formed initially with an annular shape prior to forming in a linear shape, then resume the annular shape when exposed for a length of time at internal body temperature. When the strip is deployed in the blood vessel, it is curved into an annular shape. FIG. 2 shows the view of the strip of material in FIG. 1B after it is curved into its preferred shape of deployment in the blood vessel, leaving a large inner, open area 36 for blood flow through it. The barbs are shown opened to outwardly pointing angles 37 due to bending forces so that they point toward the wall or surface of the blood vessel.

In a typical configuration, the ribbon tack may have a width of about 0.1 to 5 mm, a diameter (when curved in annular shape) of about 3-10 mm, a length (when extended linearly) of about 10 to 30 mm, and a barb height from 0.2 to 5 mm. In general, the annular band of the plaque tack has a width in the axial direction of the vessel walls that is less than its diameter, in order to minimize the amount of foreign structure to be emplaced in the blood vessel. For larger vessels and tack designs made of wire, the width/diameter ratio can be as low as 1/10 to 1/100.

Figure 3:
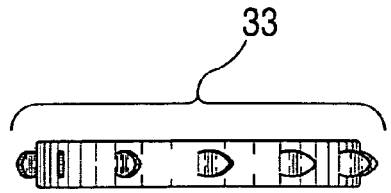
FIG. 3 is a plan view of the ribbon tack of FIG. 1B in its annular shape after deployment.
Figure 4A:
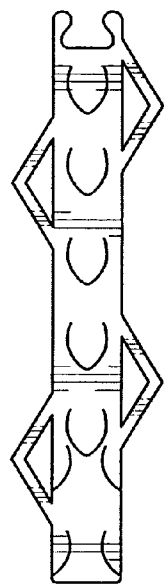
FIG. 4 is an alternative version of the ribbon tack of FIG. 1B having stabilizing wings.
Figure 4B:
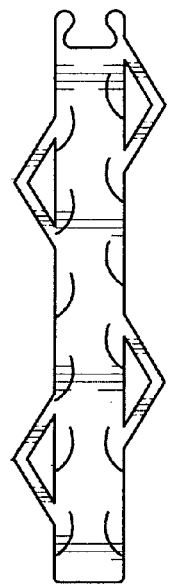
Figure 8:
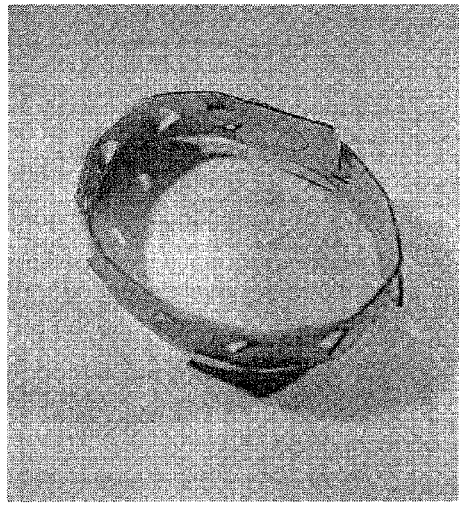
FIG. 8 is a photo image of the ribbon tack of FIG. 1B showing the tongues or cutout portions protruding at an angle from the metal strip when the tack is bent into an annular shape.
Figure 9:
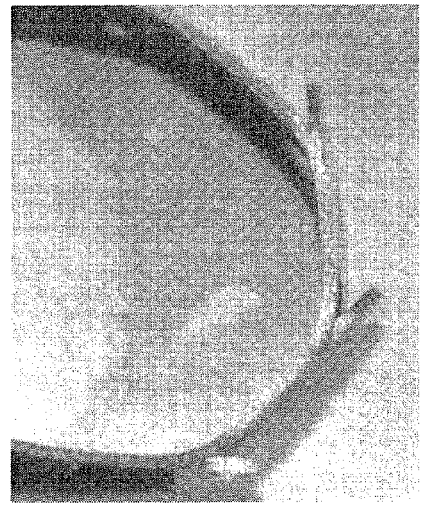
FIG. 9 is a close-up image of the anchor points of the ribbon tack of FIG. 1B.
Figure 10:
FIG. 10 is a photo image of the ribbon tack of FIG. 1B prior to installation.

FIG. 3 is a schematic diagram showing a top view of the ribbon tack bent into its annular shape. FIG. 4 shows an alternative version of the ribbon tack having stabilizing wings provided along its side edges for added lateral stability when deployed in the blood vessel. FIG. 8 shows an overhead photo image of the ribbon tack with anchors protruding at an outward angle. FIG. 9 is a close-up image of the anchors of the annular strip. FIG. 10 is an overhead image of the metal strip extended linearly when at rest.

Figures 11, 12:
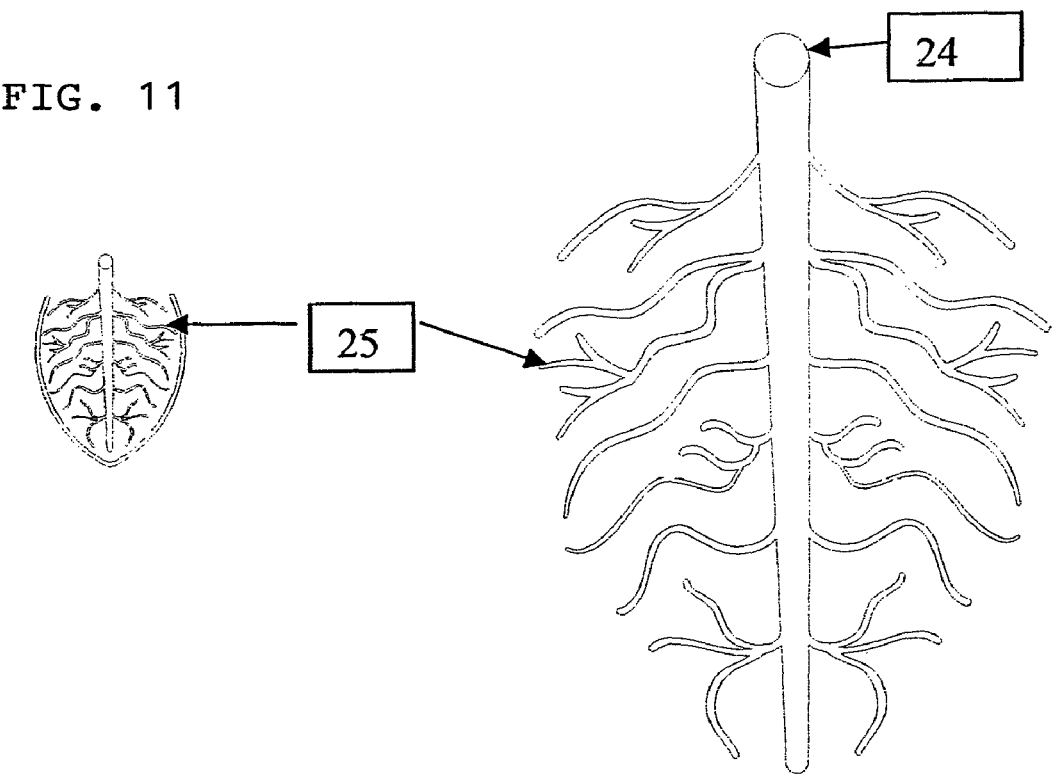
FIG. 11 illustrates a pattern of capillaries formed on the tongues of the ribbon tack of FIG. 1B for delivering plaque-growth retarding material into the plaque.
FIG. 12 is a close-up view of the capillaries formed on the tongues of the ribbon tack in FIG. 11.

FIG. 11 illustrates a pattern of capillaries 25 that may be formed by etching the surfaces of the tongues or cutout portions for delivering plaque-growth retarding material or other treatment agent where the tack is installed at the plaque accumulation site. FIG. 12 illustrates how the pattern of capillaries 25 is supplied with plaque-retarding or treatment material through a supply conduit 24. The material may be either resident within the channels prior to insertion of the tack or transferred from a reservoir on the inside of the annulus, through a hole to the outside of the component on the surface, into the anchored object, and into the tissue wall, enabling delivery of a treatment or such that enables additional preventative measures for retaining optimal blood flow. The forces that enable the transfer of the material from the inside of the annulus through the tree branches might be either capillary force or a combination of capillary and hydraulic pressure. Capillary action, capillarity, capillary motion, or wicking is the ability of a substance to draw another substance into it. The standard reference is to a tube in plants but can be seen readily with porous paper. It occurs when the adhesive intermolecular forces between the liquid and a substance are stronger than the cohesive intermolecular forces inside the liquid. The effect causes a concave meniscus to form where the substance is touching a vertical surface.

The array of barbs or anchor points is used for linking the annular band of the tack with the plaque mass or blood vessel wall. The barb is made of a sufficiently rigid material to sustain a locking relationship with the blood vessel tissue and/or to pierce the plaque and maintain a locking relationship therewith. The barb is comprised of a head disposed on a support body. Preferably, the head and support body are integral with each other and are constructed as a single piece. The barb may project at an angle of 90 degrees to the tangent of the annular band, or an acute angle may also be used.

Figure 13:
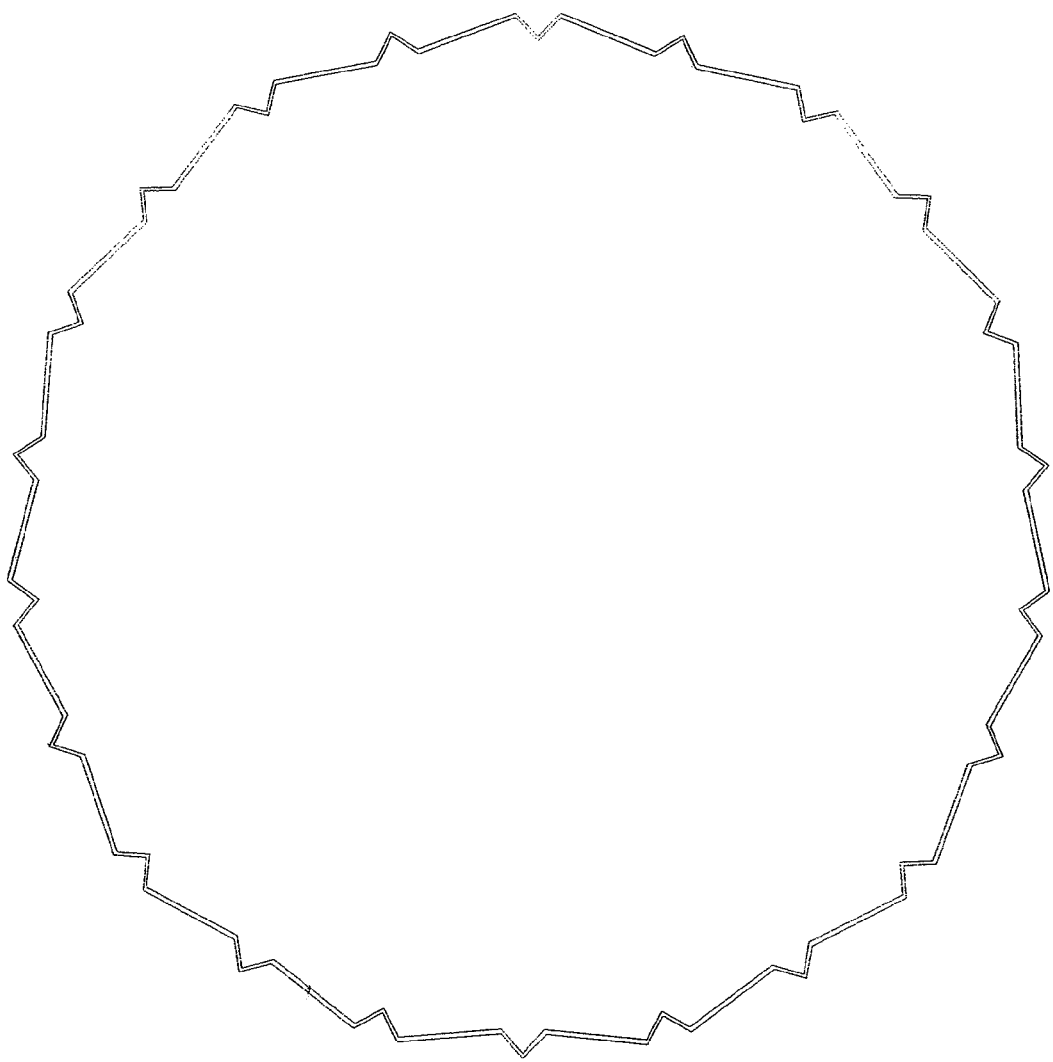
FIG. 13 is a schematic diagram of a second embodiment of a folding ring tack having inner V-shaped segments for folding and outer inverted-V-shaped points for anchoring.

Referring to FIG. 13, a second preferred embodiment of the plaque tack device is formed as a folding ring tack having inner V-shaped segments for folding alternating with outer inverted-V-shaped points. The V-shaped segments allow the ring to be radially folded to a small-diameter volume for carriage on a deployment tube on the end of the sheath. At the desired position in the blood vessel, the compressed ring tack is released from the deployment tube so that the ring springs out to its full diametral shape and the outward points act as barb or anchor points embedded into or pressed against the plaque. The folding ring tack is preferably made of metal wire material. Other options for the shape of the anchors on the outer surface may be used.

Figure 5:
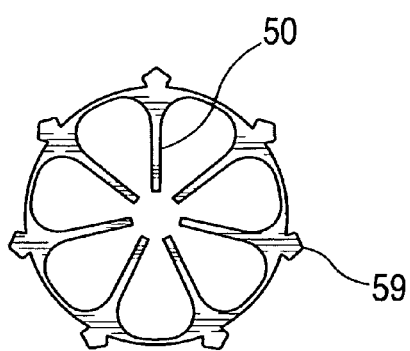
FIG. 5 is a schematic diagram of a third embodiment of flexing star tack having outward triangular anchor points and inward radial fingers.

Referring to FIG. 5, a third preferred embodiment of the plaque tack device is formed as a flexible ring tack having a pliable or hinged structure and formed with an array of radially extending points 59 on an outer side of the ring, and an array of inner radial fingers 50. The array of inner radial fingers are used to displace the points to lie horizontally flat in one axial direction when the fingers and pushed in the opposite axial direction. With the barbs or points displaced to lie horizontally flat, the flexible ring tack can be loaded on a catheter delivery tube and held down in by a cover. The fingers are then removed so that they are not present to obscure the blood vessel when the tack is installed. At the desired position, the retainer cover is displaced to release the ring tack which springs up to extend its points radially outwardly for embedding into the plaque. The body of the annular ring may have differing degrees of thickness and different designs for the fingers in the central area, such as the raised triangular anchors 59 and radial fingers 50 shown in FIG. 5.

FIGS. 7A-7D show alternative shapes for the third embodiment of FIG. 5 with a variety of different anchoring designs 72, 73, 78, 80. The fingers 76, 77 for bending the points flat for insertion are included with any of the designs. When the fingers are removed after pre-loading, and the flexible ring tack has been deployed, the inner area 74, 75 within the annular ring 79, 82 is left unobstructed.

Figure 6:
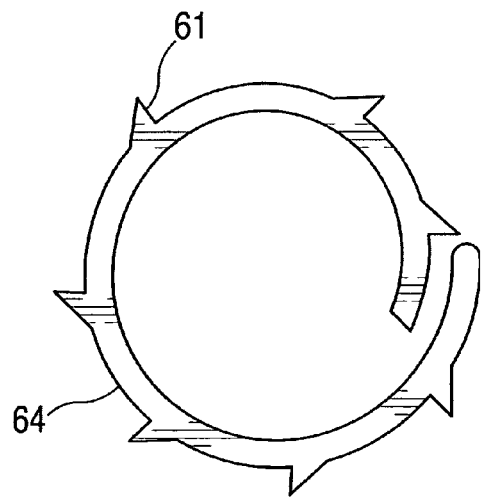
FIG. 6 is a schematic diagram of a fourth embodiment of a spiral coil tack with unjoined ends that can be pulled in opposite directions horizontally to reduce its cross-sectional diameter for insertion in the blood vessel.
Figure 7A:
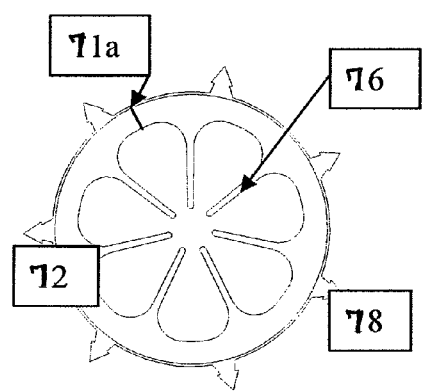
FIGS. 7A-7D show alternative shapes for the flexing star tack of FIG. 5 with a variety of different anchor point designs.
Figure 7B:
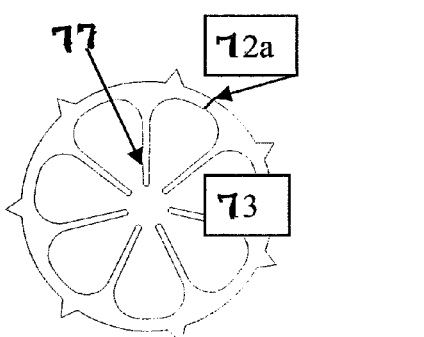
Figure 7C:
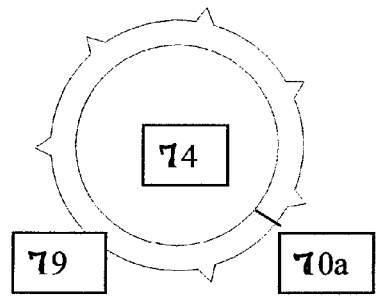
Figure 7D:
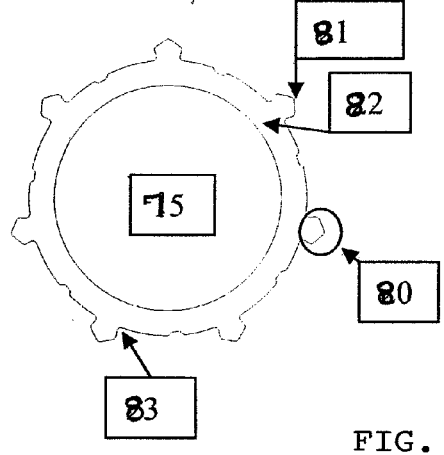

Referring to FIG. 6, a fourth preferred embodiment of the plaque tack device is formed in a coil shape 64 with ends unjoined and with barbs or points 61 on its outer periphery. The ends are pulled longitudinally in opposite directions to flatten the annular band to a spiral shape extending linearly so that it can be carried around or inside the length of a tubular sheath into the blood vessel held in place by a retainer element. At the desired position in the blood vessel, the retainer element is released to allow the tack to expand back to its full-diameter annular shape against the plaque.

Figure 14:
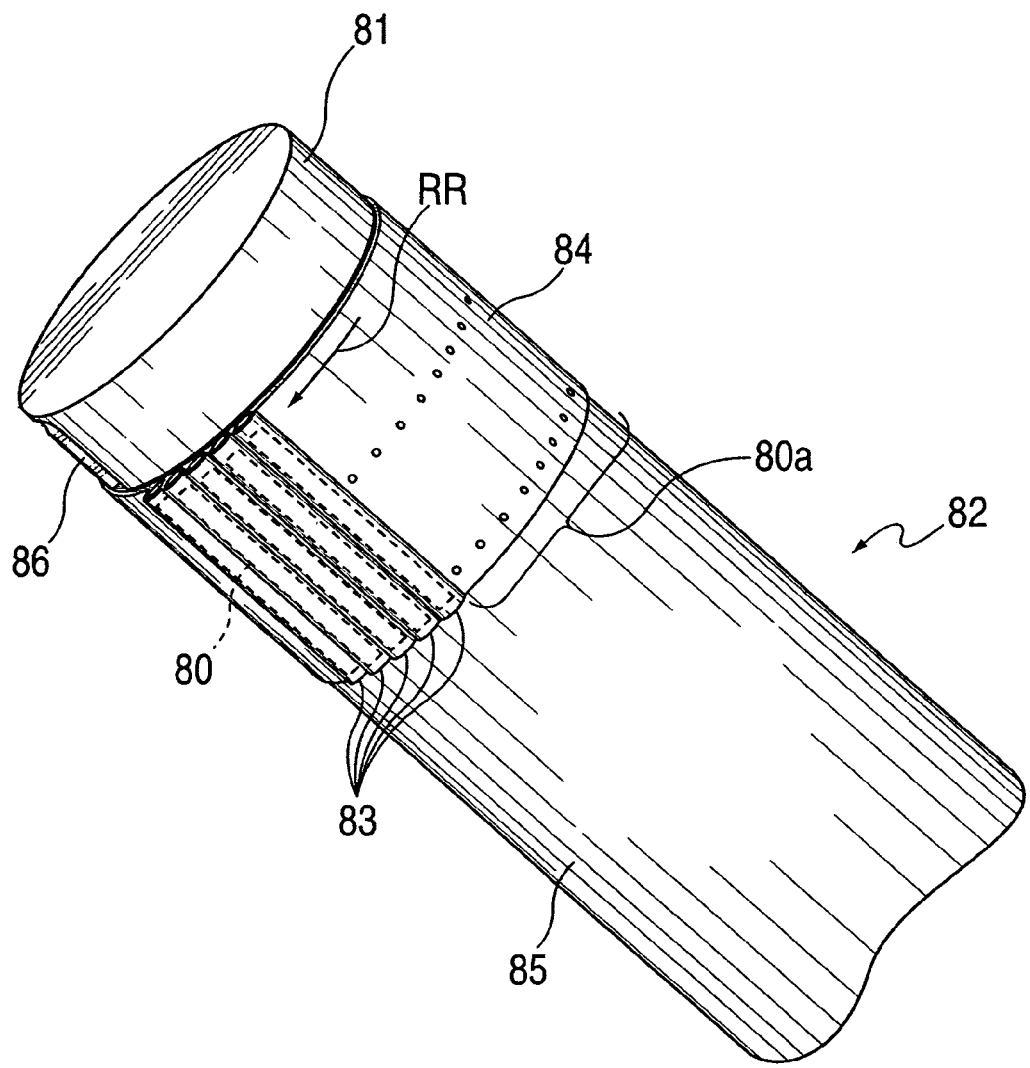
FIG. 14 is a schematic representation of the ribbon tack loaded in multiple units on the delivery head of a catheter tube for insertion into the blood vessel.
Figure 15:
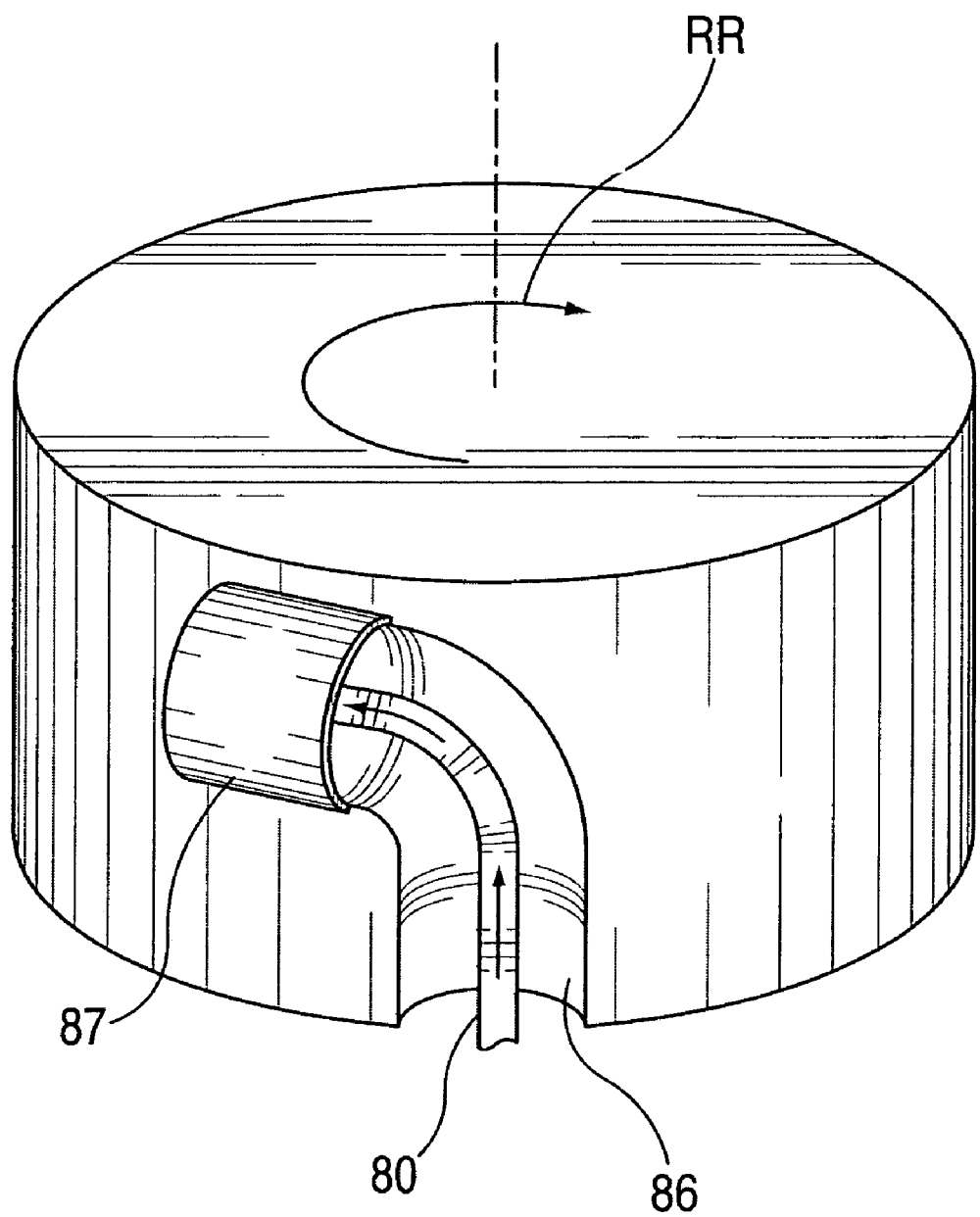
FIG. 15 is a detailed view of the delivery head for the ribbon tacks in FIG. 14.

FIGS. 14 and 15 show a preferred delivery method for the ribbon tack described above. Multiple flat ribbon strips 80 in linear form are arranged in parallel in an array 80a carried on the outer surface of the delivery head 81 of a tubular catheter 82. Each ribbon strip 80 is carried in a respective barrel 83 of a multi-barreled tack magazine 84 which wraps around the catheter, as indicated in FIG. 14. The catheter has an internal pressure chamber 85 which is loaded with saline solution or CO2 gas used to eject a ribbon strip from its barrel as it is moved by rotation of the magazine 84 in the direction RR to bring each ribbon strip in turn to an ejector position (left side of the figure) in alignment with an ejector track 86 formed in the delivery head. Pressurized fluid from the pressure chamber 85 is used to push a mover member that ejects the ribbon strip from its barrel into the ejector track 86. As shown in more detail in FIG. 15, the ejector track 86 leads into a curved outlet tunnel 87 which bends the ribbon strip towards its annular shape as the delivery head rotates. The outlet tunnel 87 curves 90 degrees from the axial direction of the catheter to the radial direction facing toward the vessel walls. This curved tunnel captures the end of the ribbon pushed into the ejector track and causes the middle part of the ribbon strip to bulge outward toward the blood vessel wall where it will lay down perpendicular to the axis of the blood vessel. The delivery head of the catheter rotates as part of the delivery mechanism. As the ribbon is being pushed out of the delivery head under hydraulic or propulsive pressure, the rotation of the delivery head allows the ribbon to be laid down in its annular shape spanning the blood vessel walls.

Figure 16:
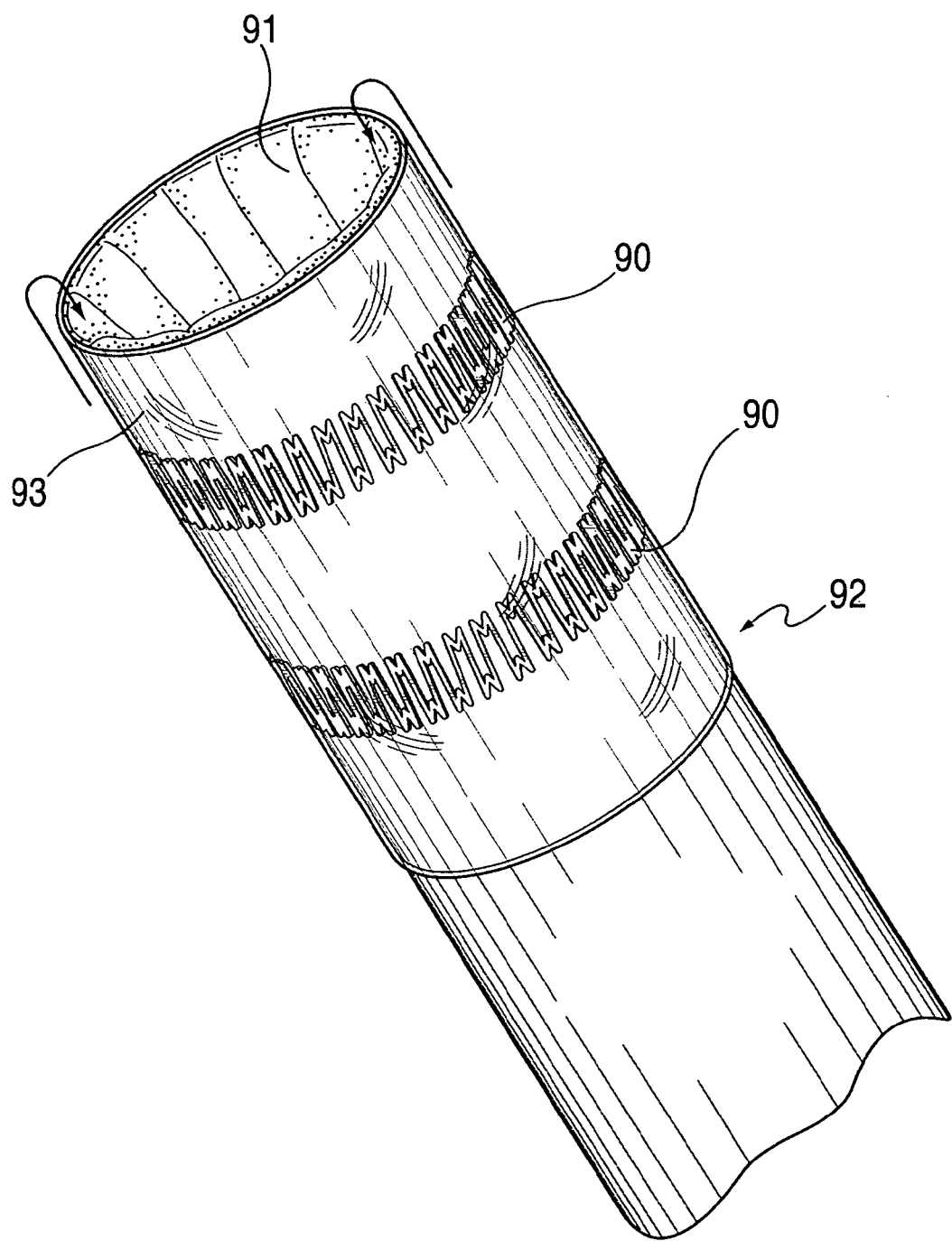
FIG. 16 is a schematic representation of the folding ring tack loaded in multiple units on the delivery head of a catheter tube with a retainer for holding them on the sheath in compressed form.
Figure 17:
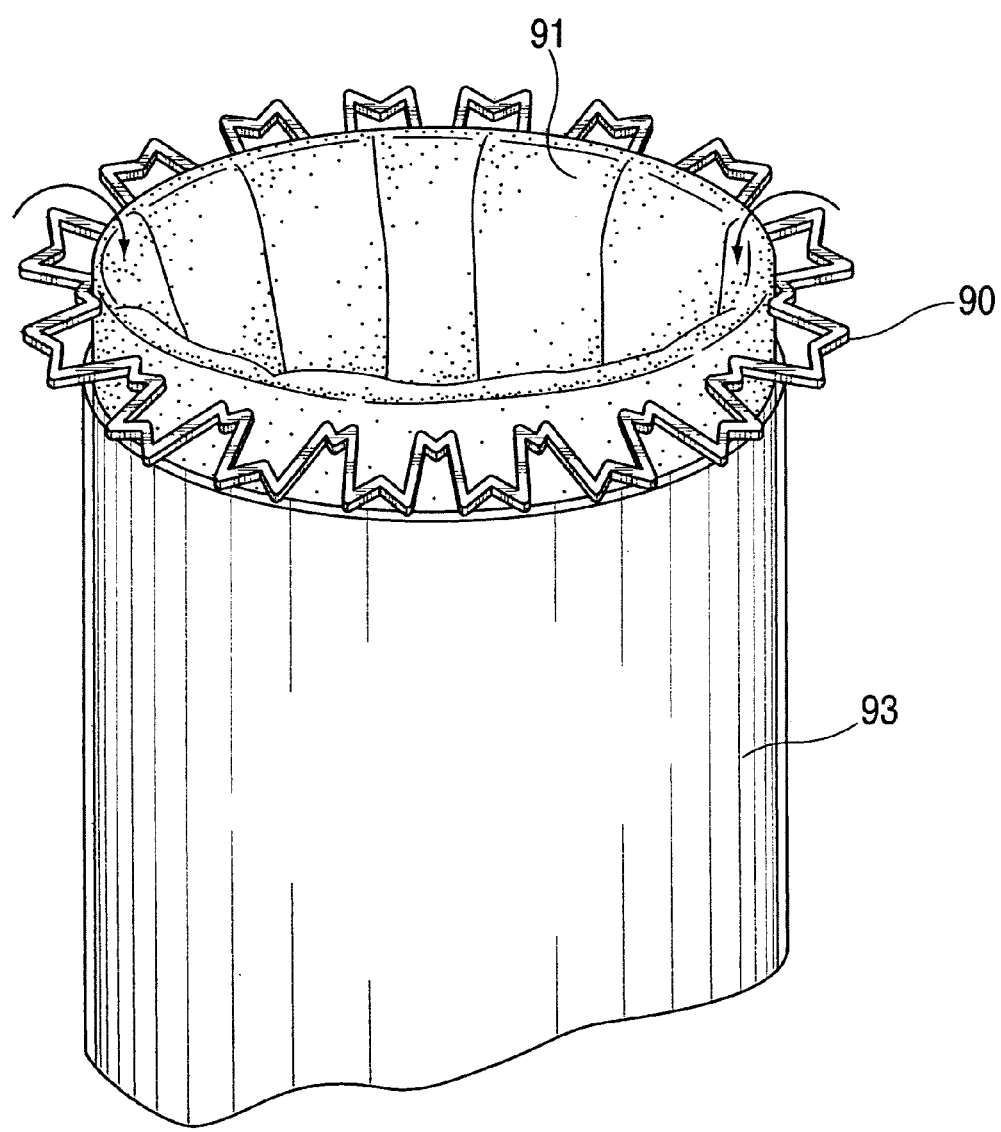
FIG. 17 is a schematic representation showing the folding ring tack partially deployed.
Figure 18:
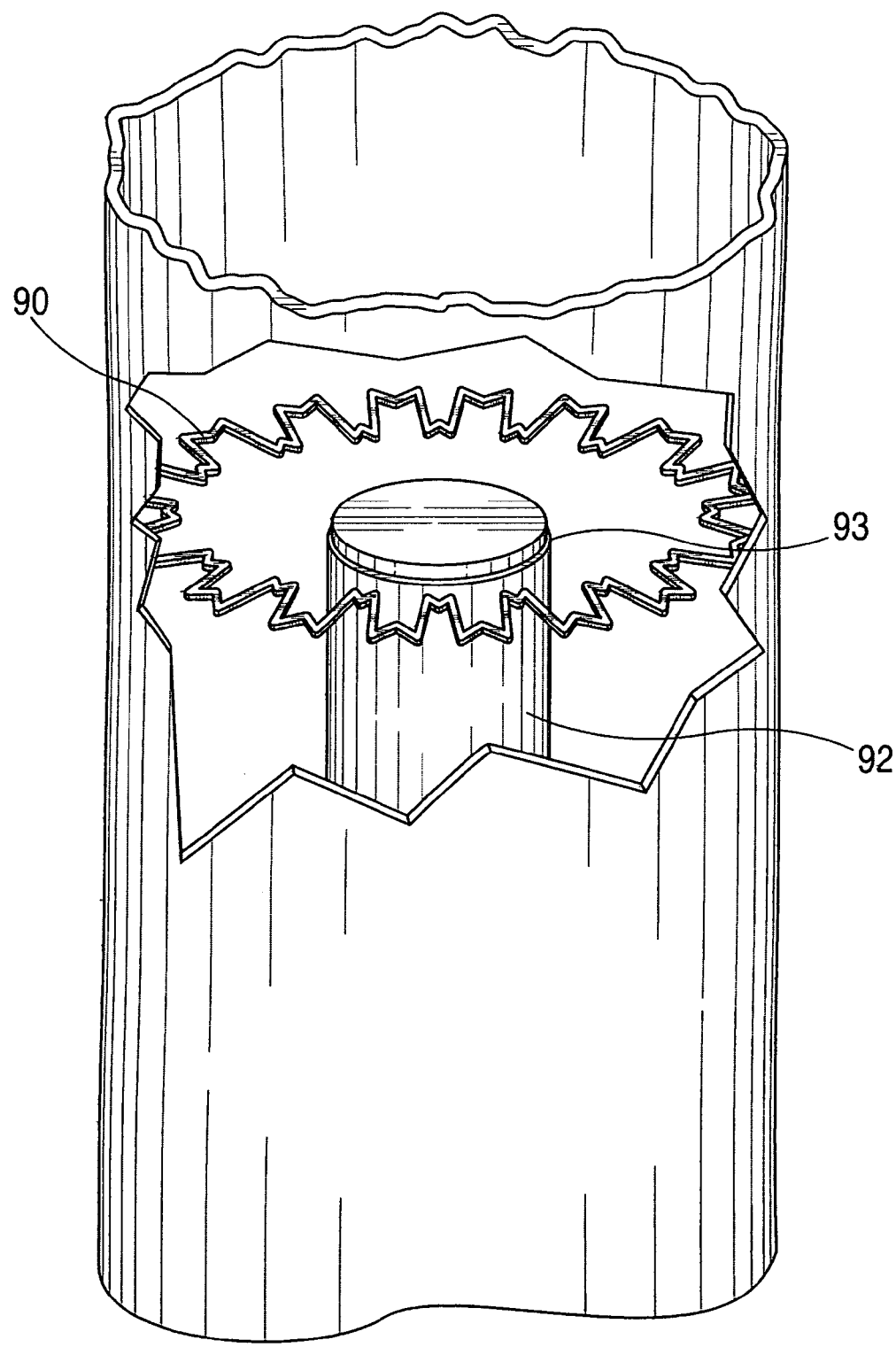
FIG. 18 is a schematic representation showing folding ring tack fully deployed in the blood vessel.

A preferred delivery method for the second described embodiment of the folding ring tack of FIG. 13 is shown in FIGS. 16, 17, and 18. The folding ring tack has an overall circular shape with inner V bends that allow it to be folded in zig-zag fashion to a compressed smaller-volume form for loading onto the delivery end of a catheter tube 92. As shown in FIG. 16, multiple units of the compressed folding ring tacks 90 are arrayed in a series on the surface of the tube. The catheter tube is hollow and lined with a fabric 91 that slides over the outer surface of the tube and is pulled over the end of the tube into its interior (direction of the U-shaped arrows). The fabric is made of a strong, durable material with low friction such as Teflon or Kevlar or like material. Multiple tacks may be loaded onto the surface of the fabric covering the outer surface of the catheter tube. The tacks are held down in their compressed, folded form by a shell or cover 93 that is telescoped over the catheter tube and prevents early deployment of the tacks. The shell may be a transparent plastic sleeve or similar structure having its end set back a small distance from the end of the catheter tube. As the fabric 91 is pulled inside the tube is pulled, the compressed tack 90 is advanced toward the end of the catheter tube. When the tack reaches the end, it is released from the shell 93, and springs back to its original shape of an annular band with outer barbs the embed or are emplaced against the plaque and blood vessel walls. FIG. 17 shows this process in action with the tack half-way deployed. The fabric 91 advancing the tack 90 is being pulled into the center of the hollow delivery tube. FIG. 18 shows the tack in place in the blood vessel after it has been separated from the delivery catheter.

The third preferred embodiment of the flexing ring tack of FIG. 5 may be deployed by a similar method as described above, by loading onto a similar sliding fabric carrier which is pulled over the outer surface of a catheter tube, with a shell sleeved over the tube for retaining the tacks from deployment until each reaches the end of the tube.

Figure 19A:
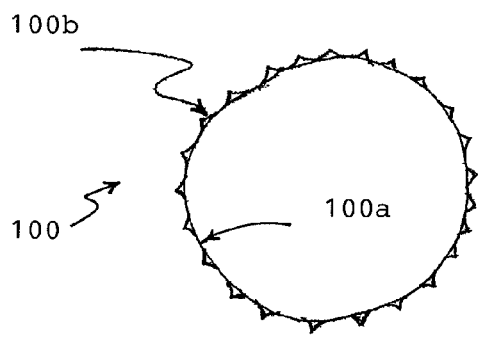
FIG. 19A shows a fifth embodiment of a wire mesh tack in end view.
Figure 19B:
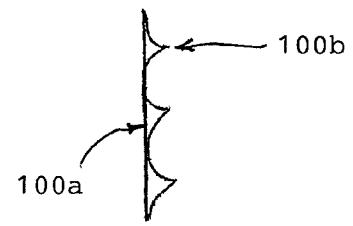
FIG. 19B shows it in side view.
Figure 19C:
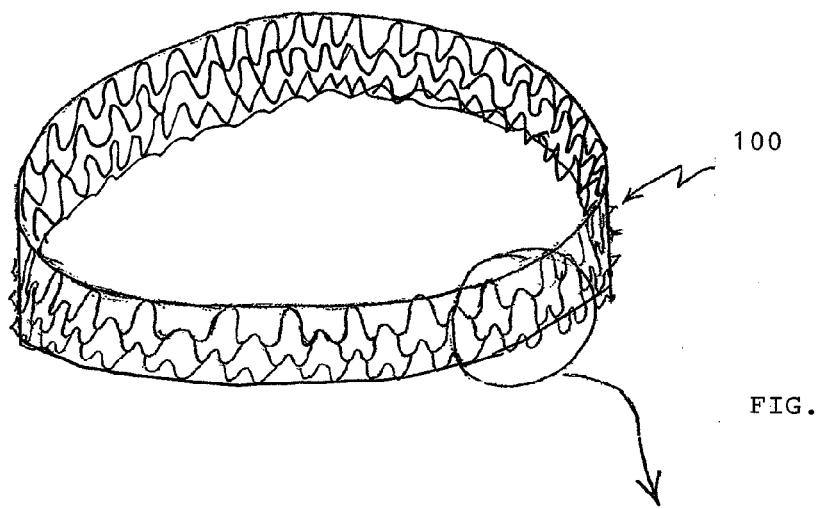
FIG. 19C shows the wire mesh tack in perspective.
Figure 19D:
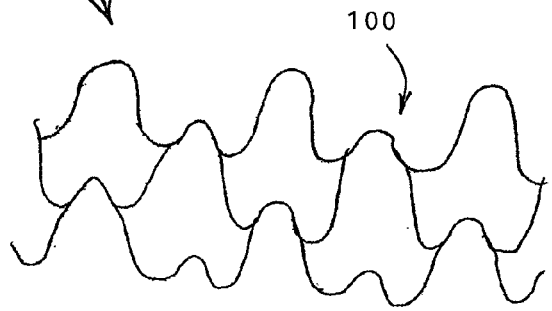
FIG. 19D shows a section of the wire mesh tack in a detailed view.
Figure 20:
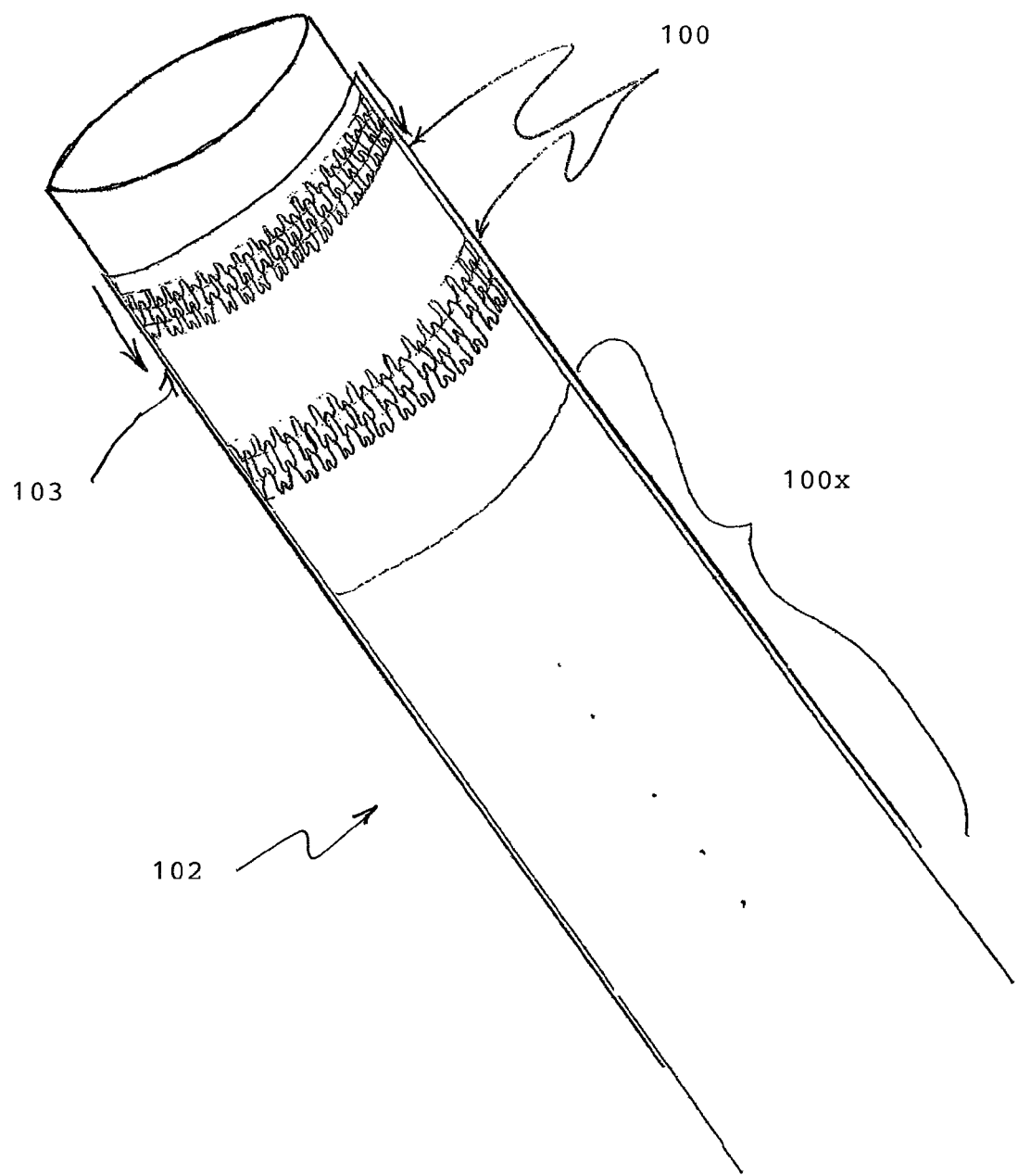
FIG. 20 is a schematic representation showing multiple units of the wire mesh tack loaded on a catheter delivery tube.
Figure 21:
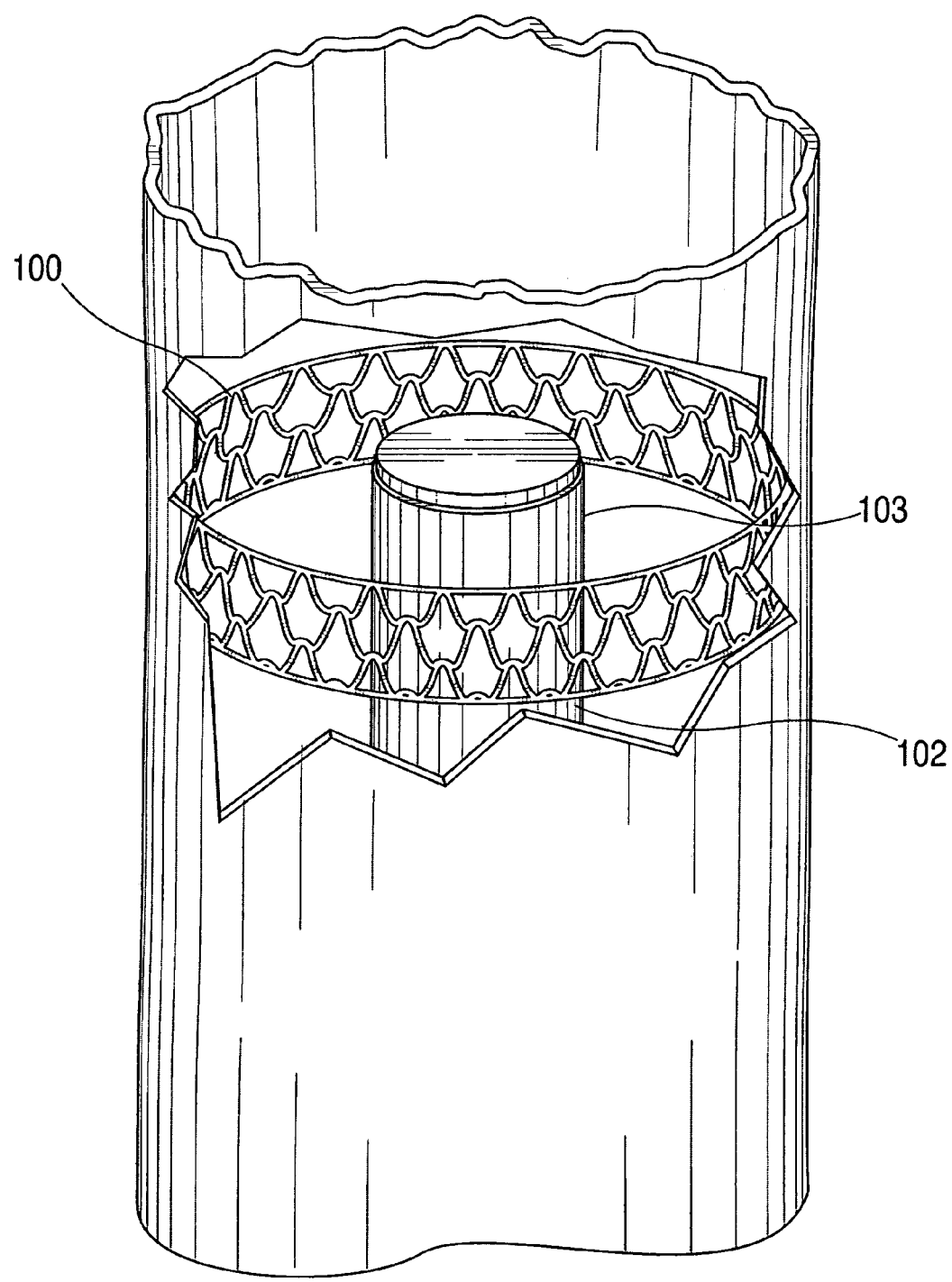
FIG. 21 is a schematic representation showing the wire mesh tack released from the delivery head and fully expanded in the blood vessel.

A fifth embodiment of the plaque tack in the form of a wire mesh tack is illustrated in FIGS. 19A-D, and its manner of deployment in FIGS. 20 and 21. In FIG. 19A, the wire mesh tack is shown in end view having an annular band 100a formed of interleaved wire mesh, and outer points or barbs 100b. The wire mesh tack is made of thin metal wire which is looped and interleaved in a mesh that is welded, soldered, looped and/or linked together into the desired mesh shape. FIG. 19B shows the wire mesh tack in side view with barbs projecting from the annular band 100a. The barbs on its outward surface will contact and embed into the wall of the blood vessel. FIG. 19C shows the wire mesh tack at rest in its fully expanded state in perspective view, and FIG. 19D shows a section of the wire mesh tack in a detailed view. The intermeshed pattern formed by the wire mesh is specifically designed so that it can be compressed radially inward to a smaller-volume size for loading on a catheter delivery device to be inserted into the blood vessel.

A preferred method of delivery for the wire mesh tack is shown in FIG. 20. Multiple wire mesh tacks 100 are compressed to its smaller-volume size and loaded onto the surface of a catheter delivery tube 102 in an array 100x over a given length of the tube. As in the previously described delivery method, a cover or shell 103 is sleeved over the surface of the tube to hold the tacks in their compressed state and prevent early deployment of the tacks. As the cover 103 is withdrawn down the length of the tube, each wire mesh tack in turn is released and expands to its full-volume size. FIG. 21 shows the wire mesh tack 100 expanded and deployed in the blood vessel.

Figure 22:
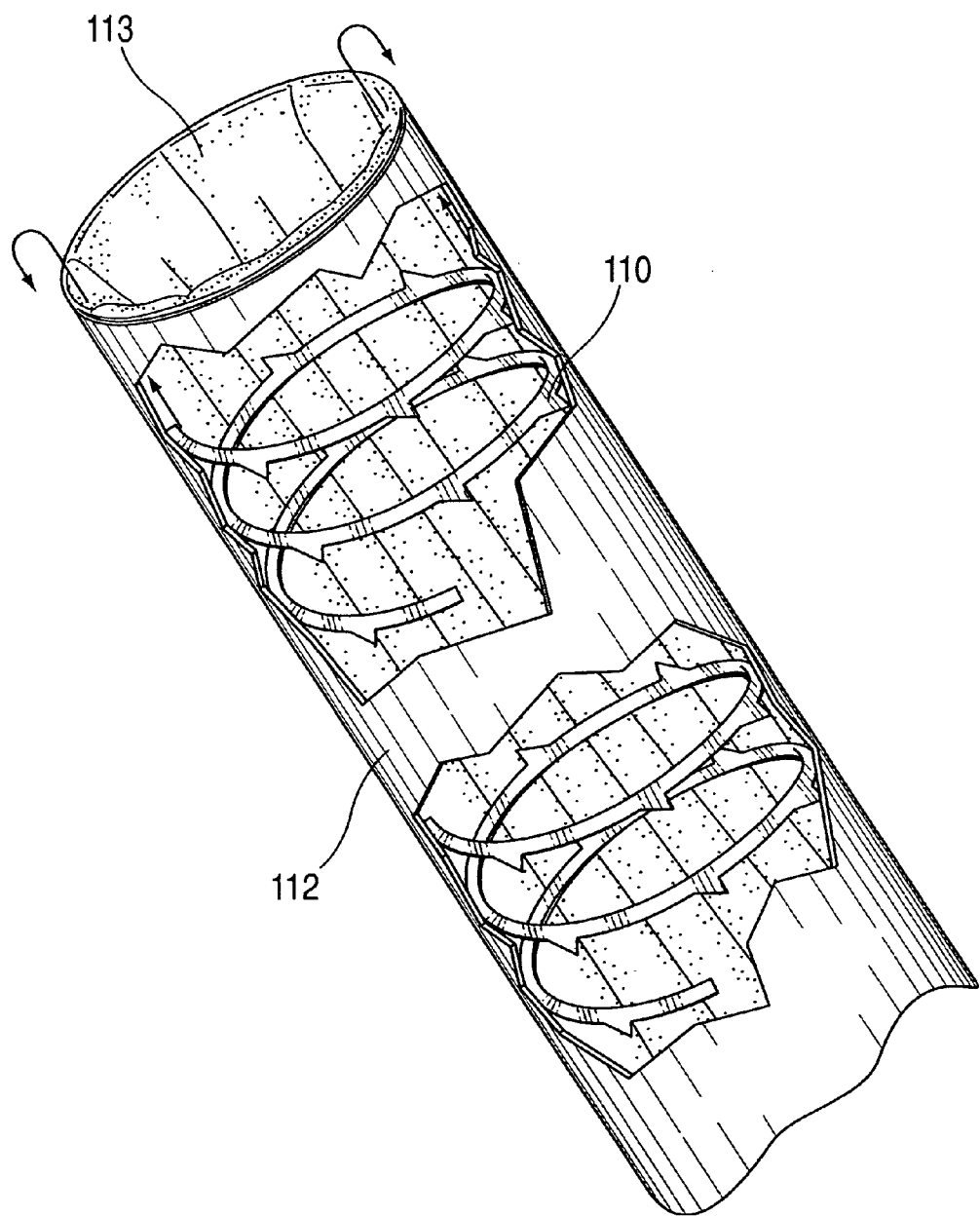
FIG. 22 is a schematic representation the spiral coil tack loaded in multiple units on the delivery head of a sheath and held down by a retainer cover.
Figure 23:
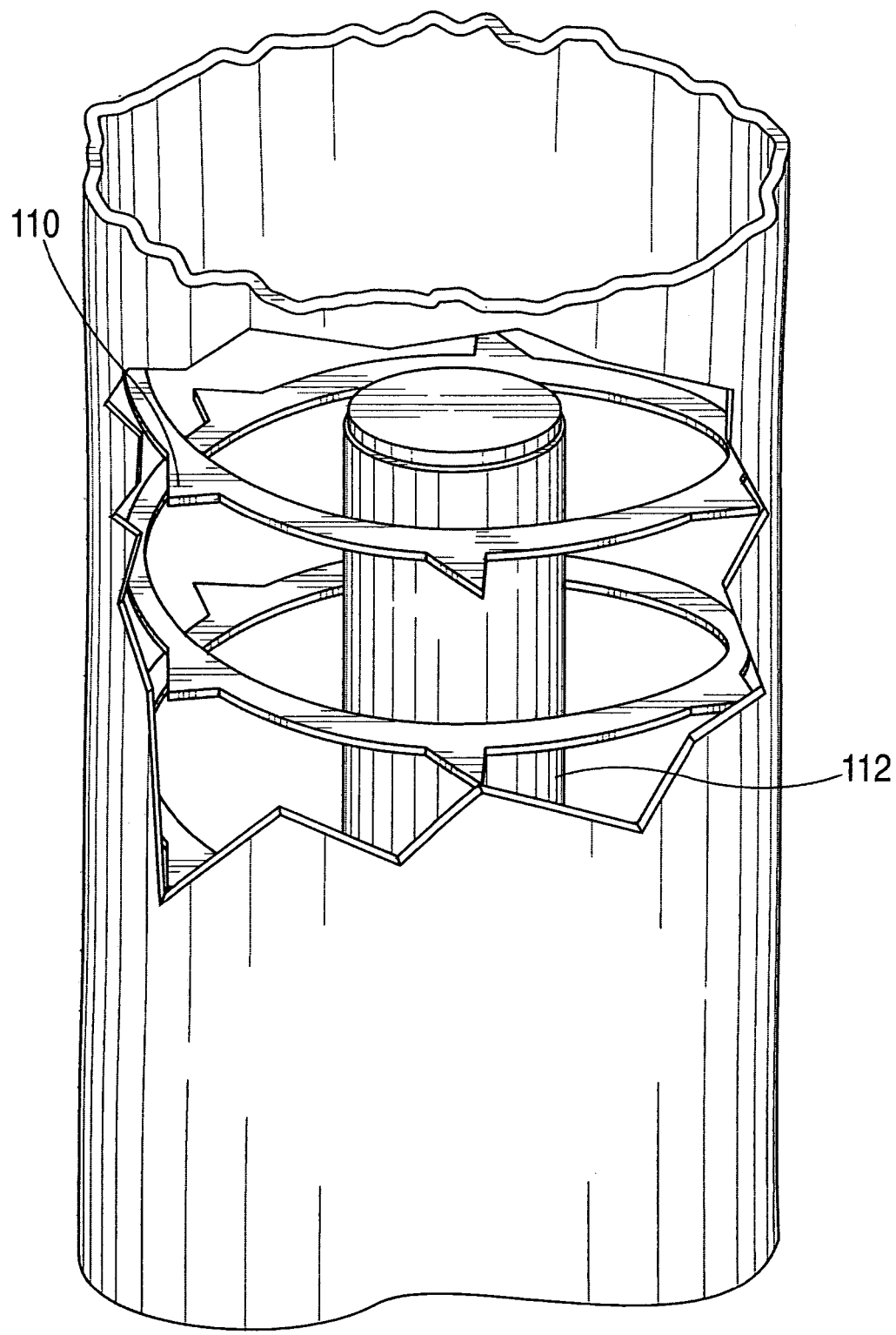
FIG. 23 is a schematic representation showing the spiral coil tack released from the delivery head and fully expanded in the blood vessel.

A preferred delivery method for the fourth described embodiment of the spiral coil tack of FIG. 6 is illustrated in FIGS. 22 and 23. The coil shaped tack in FIG. 6 is formed with barbs and a band with unjoined ends that may or may not have a taper with a varying degrees of thickness along its length. This design is uncoiled in its rest state and looks like a "broken" circle. The coil tack can be compressed to a fraction of its at-rest diameter by pulling its ends in opposite linear directions to form a tight spiral that occupies a smaller-diameter volume so that it can be inserted into the blood vessel. When released it can expand to several times the diameter of its spiral form. FIG. 22 shows multiple units of spiral coil tacks 110 loaded in the interior of the catheter delivery tube 112. When the tack is compressed, it occupies several spiral turns and it spaced out longitudinally. In this case, the delivery catheter is lined with fabric 113 slidable on its interior surface over the end of the tube to its outside (indicated by the pair of U-shaped arrows). As the fabric is pulled through the center of the tube, the tack is advanced toward the end of the delivery catheter. When the tack reaches the end of the delivery catheter, the tack is released from the tube and re-expands to its full size to be deployed into the wall of the blood vessel. FIG. 23 shows the tack deployed in the blood vessel.

In the embodiments described above, the preferred plaque tack device may be made from Nitinol, silicon composite (with or without an inert coating), polyglycolic acid, or some other superelastic material. The anchors can have a preferred length of 0.2 mm to 5 mm. The strip of material can be created from ribbon, round or rectangular wire or a sheet of material processed through photolithographic processing, laser or water cutting, chemical etching or mechanical removal of the final shape, or the use of bottom up fabrication, for instance chemical vapor deposition processes, or the use of injection modeling, hot embossing, or the use of electro or electroless-plating. It may be fabricated from metal, plastic, ceramic, or composite material.

The plaque tack is designed to be inherently self-aligning, i.e., its mechanical installation can accommodate small misalignments. This serves to facilitate placing the tacks in specific locations within diseased blood vessels. With respect to the piercing barb that has a pointed shape, it can be used to embed in objects having irregular surfaces such as plaque or dissected or damaged artery surfaces. After deployment of the plaque tack, the surgeon has the option of placing an angio-plasty balloon at the site of the tack and inflating the balloon to press the anchor or anchors into the wall of the blood vessel.

It is to be understood that many modifications and variations may be devised given the above description of the principles of the invention. It is intended that all such modifications and variations be considered as within the spirit and scope of this invention, as defined in the following claims.

The invention claimed is:

1. A device for holding plaque against blood vessel walls in treating atherosclerotic occlusive disease, comprising:
    a thin, annular band of durable, flexible material having a plurality of barbs on its outer annular periphery, said annular band being dimensioned and designed to be applied with an outward expansion force against the plaque to press and hold it against the blood vessel walls,
    wherein each of said barbs is formed with a head having a sharp point integrally formed on a support body, and is made of a sufficiently rigid material so that, when the outward expansion force is applied, they pierce the plaque and maintain a locking relationship with the blood vessel walls;

wherein said annular band is formed as a flexible ring of pliable material with an array of outer barbs on an outer side of the ring, and an array of inner radial fingers, wherein the array of inner radial fingers are used to displace the outer barbs to lie horizontally flat in one axial direction when the fingers are pushed in the opposite axial direction.

2. A device according to claim 1, wherein the annular band has a width in the axial direction of the blood vessel walls that is less than its diameter in order to minimize the emplacement of foreign structure in the blood vessel.

3. A device according to claim 1, wherein the annular band is designed to be compressed, folded, or plied to take up a smaller-diameter volume for insertion into the blood vessel, wherein it can be released to expand, unfold or unply to its full diametral size within the blood vessel walls.

4. A device according to claim 1, formed as a folding ring tack having V-shaped segments alternating with inverted-V-shaped points, said V-shaped segments enabling said ring tack to be folded to a smaller-diameter volume for insertion into a blood vessel.

5. A device according to claim 1, wherein said barbs are formed with conduits for enabling plaque treatment material to be conducted to the surface of the barbs through capillary channels.

6. A device according to claim 1, made from a material selected from the group consisting of: Nitinol; silicon composite; a superelastic material; a metal; a plastic; a ceramic; and a composite material.

7. A device according to claim 1, wherein the barbs have a barb penetration into the plaque and/or vessel walls in the range of about 0.2 to 5 millimeters.

* * * * *